(12) United States Patent
Eaton, Jr. et al.

(10) Patent No.: US 8,346,572 B2
(45) Date of Patent: Jan. 1, 2013

(54) PROVIDING CLINICAL INFORMATION TO CLINICIANS

(75) Inventors: James D. Eaton, Jr., Gardner, KS (US); David L. Compton, Lenexa, KS (US); Justin Nelson, Merriam, KS (US); Paul Cannon, Kansas City, MO (US); Mark Allen Nolte, Lee's Summit, MO (US)

(73) Assignee: Cerner Innovation, Inc., Lenexa, KS (US)

(*) Notice: Subject to any disclaimer, the term of this patent is extended or adjusted under 35 U.S.C. 154(b) by 380 days.

(21) Appl. No.: 12/612,426

(22) Filed: Nov. 4, 2009

(65) Prior Publication Data

US 2011/0106560 A1  May 5, 2011

(51) Int. Cl.
*G06Q 10/00* (2012.01)
*G06Q 50/00* (2012.01)
(52) U.S. Cl. .................. 705/2; 705/3; 701/300
(58) Field of Classification Search .................. 705/2–3
See application file for complete search history.

(56) References Cited

U.S. PATENT DOCUMENTS

| 2006/0143041 | A1* | 6/2006 | Tipirneni ............ 705/2 |
| 2006/0181424 | A1* | 8/2006 | Graves et al. ............ 340/573.1 |
| 2009/0265106 | A1* | 10/2009 | Bearman et al. ............ 701/300 |

* cited by examiner

*Primary Examiner* — Lena Najarian
*Assistant Examiner* — Minnah Seoh
(74) *Attorney, Agent, or Firm* — Shook, Hardy & Bacon L.L.P.

(57) ABSTRACT

Systems, methods, and computer-readable media for providing clinical information to clinicians are provided. In embodiments, a patient's electronic health record is accessed to identify that a first clinician has requested a consult with a second clinician. Each clinician is associated with a clinician identifier that is identified by a plurality of sensors. A location for both the first and second clinician is received from the plurality of sensors. A determination is made whether the first and second clinicians are near one another. Upon determining that the first and second clinicians are near one another, a notification is presented to the first clinician. Such tracking of clinician location helps avoid missed opportunities and provides efficient communication among clinicians.

8 Claims, 5 Drawing Sheets

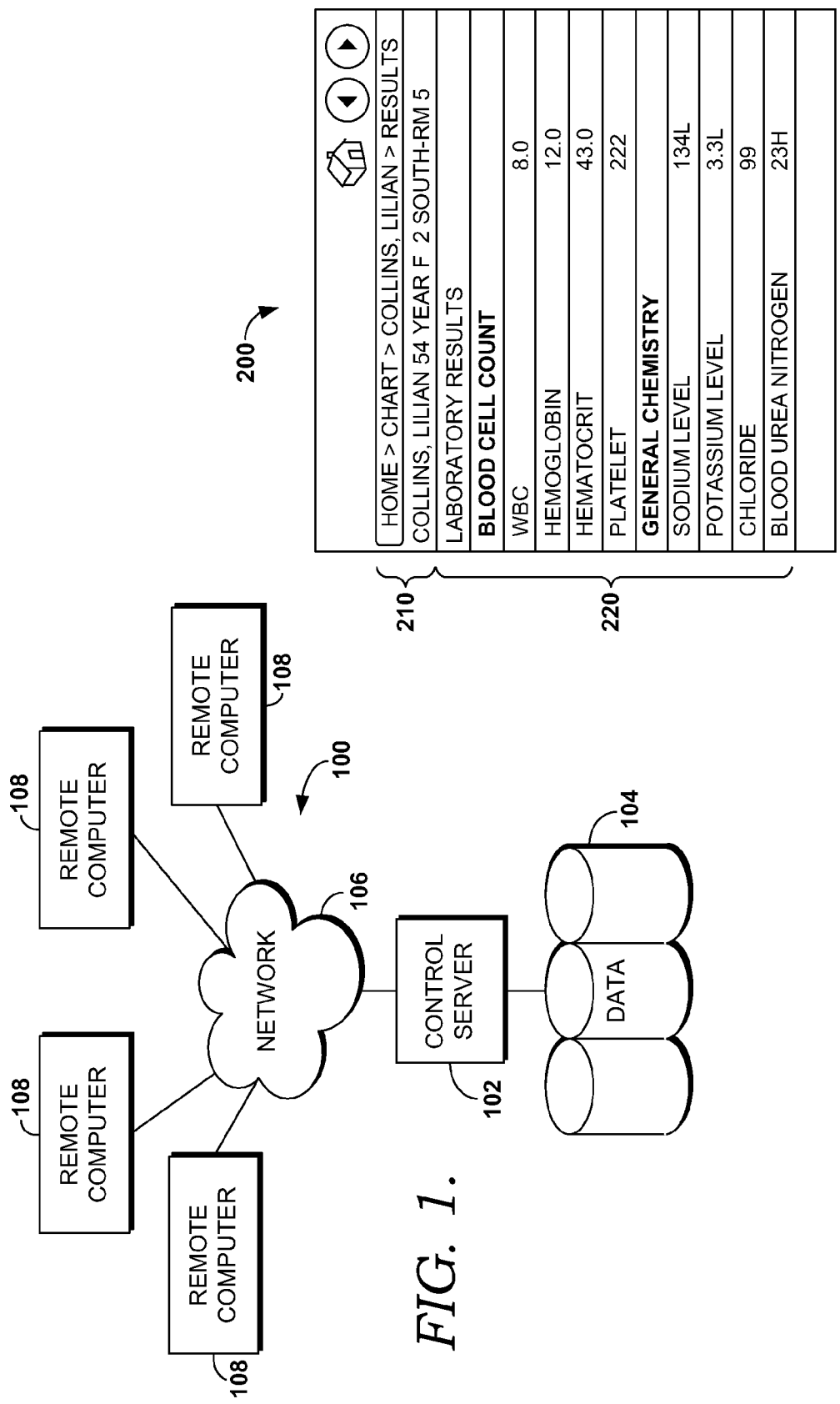

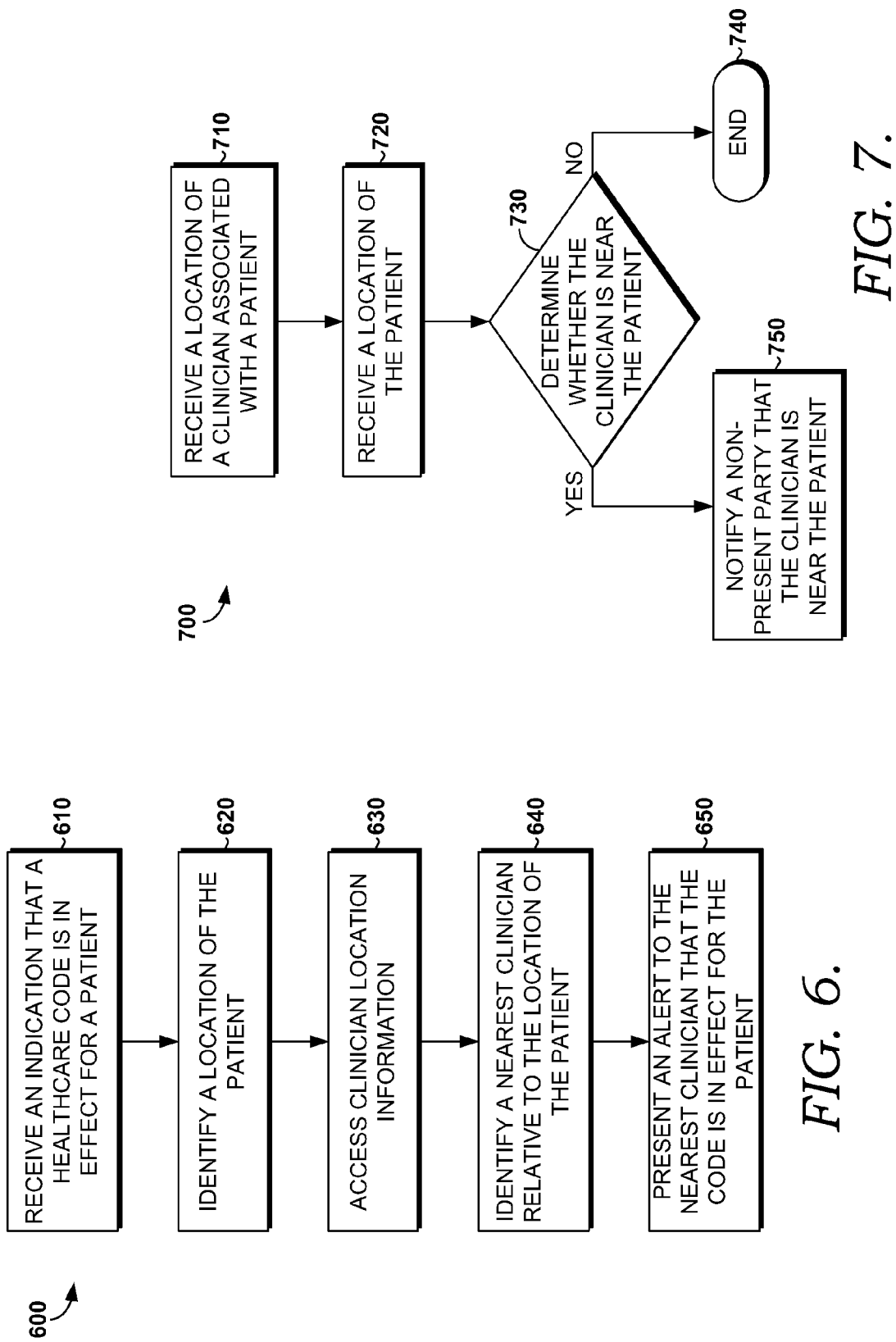

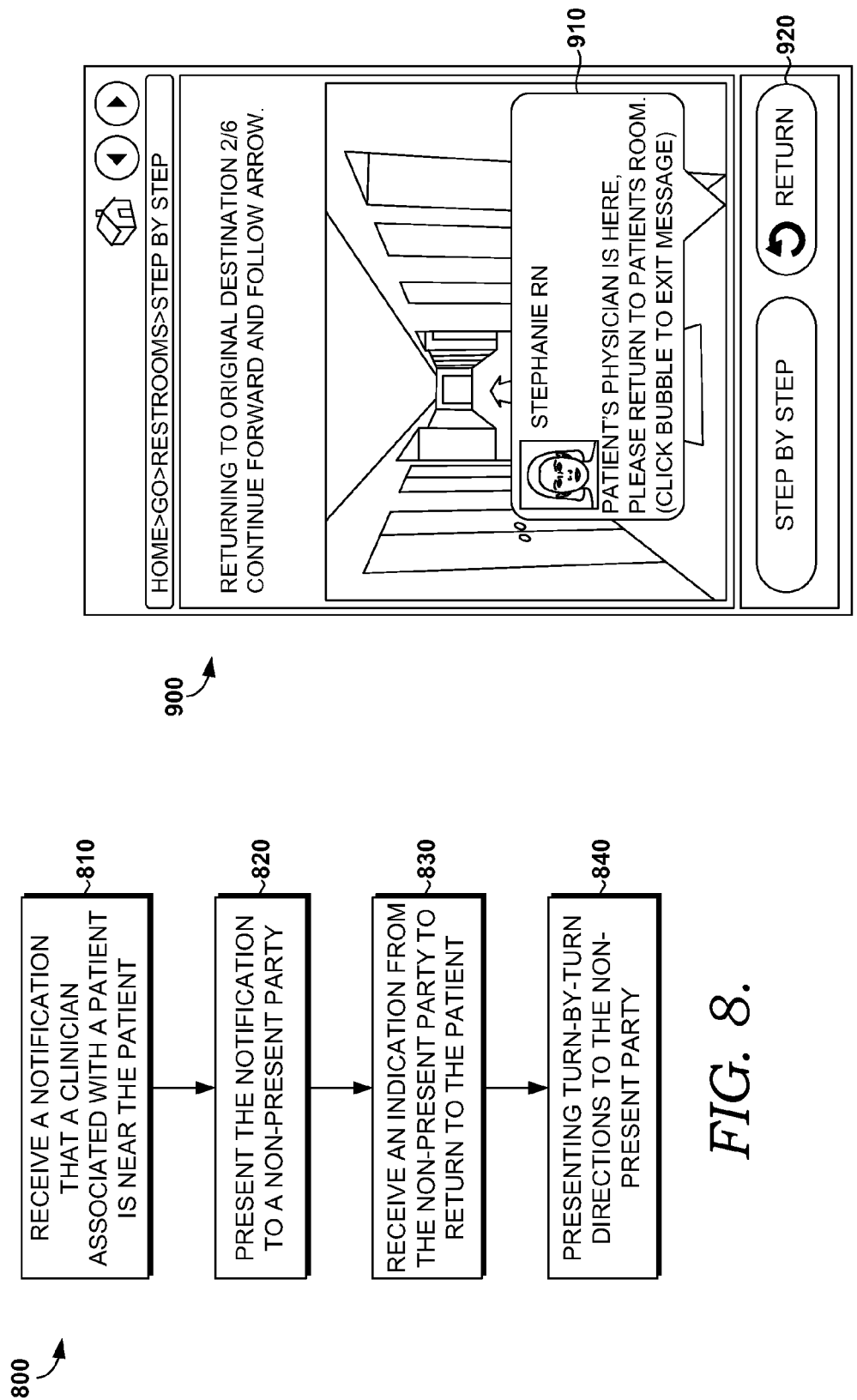

PROVIDING CLINICAL INFORMATION TO CLINICIANS

CROSS-REFERENCE TO RELATED APPLICATIONS

This application is related by subject matter to the invention disclosed in the commonly assigned application U.S. application Ser. No. 12/612,421, entitled "Optimization of a Clinical Experience," filed on even date herewith. The aforementioned application is herein incorporated by reference in its entirety.

BACKGROUND

Clinical integration into a paperless chart, i.e., an electronic health record (EHR), increases efficiency by allowing an up-to-date view of the EHR. Such an up-to-date view includes information regarding orders that are input by clinicians, consultations requested by clinicians, test results, and the like. Computing devices may notify clinicians, patients, family members, or the like of clinical events. Clinical events include, but are not limited to, non-invasive procedures, surgical procedures, tests, evaluations, examinations, consultations, or the like.

Clinicians are often waiting on clinical events, or notifications thereof, to create a treatment plan. For example, a clinician may wait on a test result before ordering further treatment. Additionally, family members and/or patients may also be affected by clinical events. For instance, family members will often leave the room of a patient but want to be notified when the clinician returns so that they may return to the patient's room. Currently, family members are not included in the clinical experience. Thus, access to clinical event information is desirable for clinicians to have the most up-to-date information and for patients and family members to be included in the clinical experience.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

The present invention relates to computing environments. More particularly, embodiments of the present invention relate to methods for use in, e.g., a patient care computing environment. Further embodiments of the present invention relate to a mobile device for providing clinical information to clinicians in accordance with one or more of the described methods. Additional embodiments of the present invention relate to a mobile device for optimizing a clinical experience.

In one embodiment, a set of computer-useable instructions providing a method for providing clinical information to clinicians is illustrated. The method includes identifying in a patient's electronic health record that a first clinician treating the patient has requested a consult with a second clinician treating the patient. The location of both the first clinician and the second clinician is received by way of a first clinician identifier and a second clinician identifier that is tracked via a plurality of sensors in a healthcare environment. A determination is made whether the location of both the first clinician and the second clinician are near one another. The determination is based on the proximity of the sensors that identified the location of both the first and the second clinician. Based upon a determination that the location for the first clinician and the location for the second clinician are near one another, a notification is presented to the first clinician that includes the location of the second clinician.

In another embodiment, a set of computer-useable instructions providing a method for providing clinical information to clinicians is illustrated. An indication is received that a first clinician has input a healthcare order for a patient. One or more tangible items are determined to fulfill the healthcare order. Upon determining one or more tangible items to fulfill the healthcare order, a location for each of the one or more tangible items to fulfill the healthcare order is determined. A second clinician is notified of the healthcare order and a location of the tangible item to fulfill the healthcare order. The location of the one or more tangible items is the location of the tangible item that is nearest to the second clinician. The second clinician is routed to the location of the tangible item to fulfill the healthcare order.

In another embodiment, a set of computer-useable instructions providing a method for providing clinical information to clinicians is illustrated. An indication is received that a healthcare code is in effect for a patient. The location of the patient is determined and clinician location information is accessed. The locations of both the patient and the clinicians are based on a patient identifier and clinician identifiers that are identified by a plurality of sensors in the healthcare environment. Based on the clinician location information, the nearest clinician to the location of the patient is determined. An alert is presented to the nearest clinician that the code is in effect for the patient.

In another embodiment, a set of computer-useable instructions providing a method for optimizing a clinical experience is illustrated. A location of a clinician associated with a patient and a location of the patient are received. The location of both the clinician and the patient is based on a clinician identifier and a patient identifier that are identified by a plurality of sensors within a healthcare environment. A determination whether the clinician is near the patient is made. The determination is based on the proximity of a sensor that identified the patient identifier to a sensor that identified the clinician identifier. Upon determining that the clinician is near the patient, a notification indicating that the clinician is near the patient is displayed to a non-present party via a mobile device.

In another embodiment, a set of computer-useable instructions providing a method for optimizing a clinical experience is illustrated. A notification that a clinician associated with a patient is near the patient is received. The notification is presented to a non-present party and includes a selectable return indicator to return to the patient. An indication is received from the non-present party to return to the patient. Turn-by-turn directions are presented to the non-present party to return to the patient.

In yet another embodiment, a handheld computing device for optimizing a clinical experience is illustrated. The handheld computing device includes one or more graphical user interfaces for displaying location information including displaying navigational directions of a healthcare environment and identifying points of interest external of the healthcare environment. The handheld computing device also includes one or more graphical user interfaces for displaying clinician information including notifying a user of clinical events, displaying alerts to the plurality of users, notifying clinicians of an order that has been input into a patient's electronic health record, and identifying one or more tangible items required to fulfill the order. The handheld computing device also includes a communication component for communicating messages between a plurality of users.

Additional objects, advantages, and novel features of the invention will be set forth in part in the description which follows, and in part will become apparent to those skilled in the art upon examination of the following, or may be learned by practice of the invention.

BRIEF DESCRIPTION OF THE DRAWING

The present invention is described in detail below with reference to the attached drawing figures, wherein:

FIG. 1 is a block diagram of an exemplary computing environment suitable for use in implementing the present invention;

FIG. 2 is an illustrative graphical user interface display of an electronic health record being accessed and reviewed, in accordance with embodiments of the present invention;

FIG. 6 is a flow diagram illustrating a third exemplary method for providing clinical information to clinicians, in accordance with embodiments of the present invention;

FIG. 7 is a flow diagram illustrating a first exemplary method for optimizing a clinical experience, in accordance with embodiments of the present invention;

FIG. 8 is a flow diagram illustrating a second exemplary method for optimizing a clinical experience, in accordance with embodiments of the present invention; and FIG. 9 is an illustrative graphical user interface display of a notification that a clinician is near a patient, in accordance with embodiments of the present invention.

DETAILED DESCRIPTION

Figure 3:
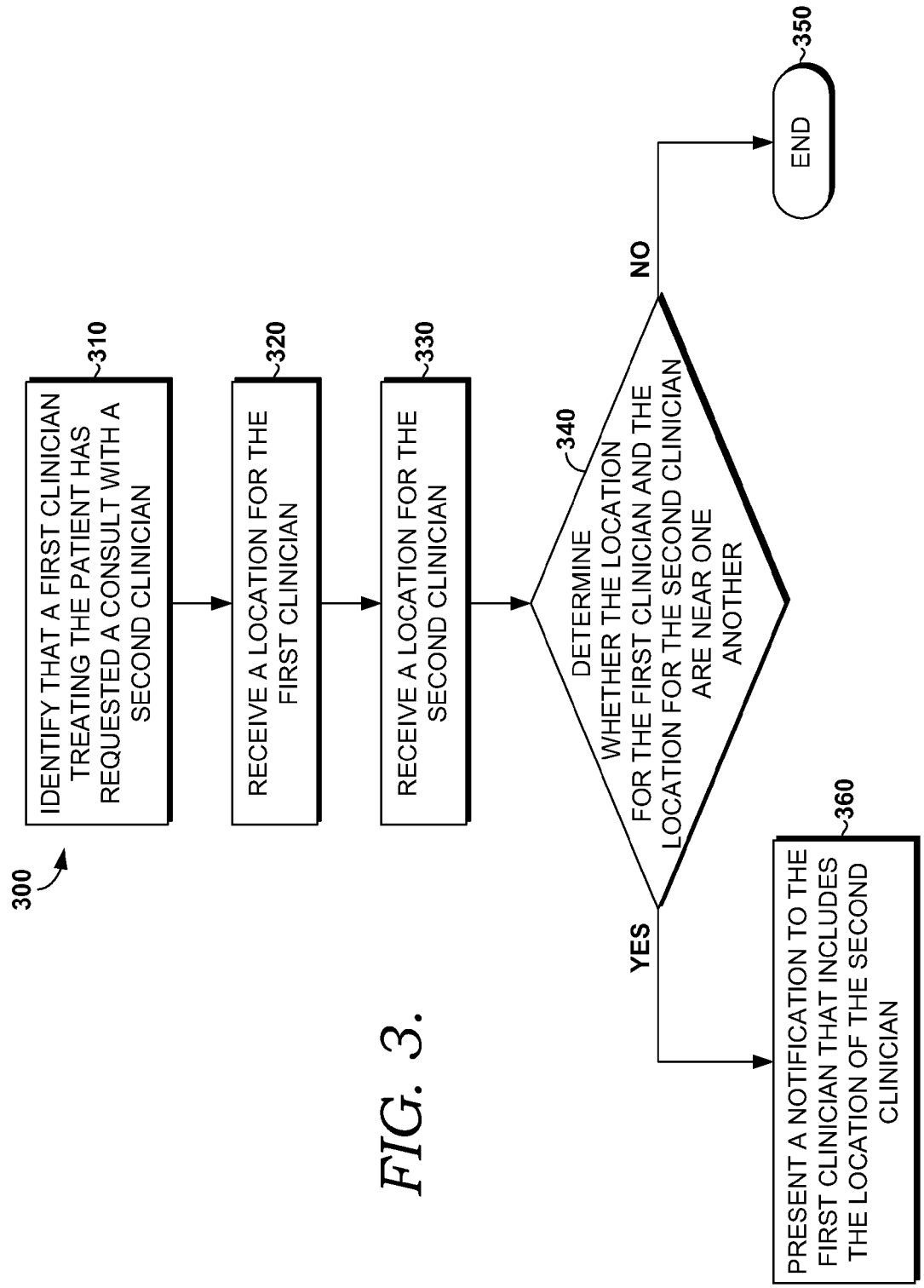
FIG. 3 is a flow diagram illustrating a first exemplary method for providing clinical information to clinicians, in accordance with embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Referring now to the drawings in general, and initially to FIG. 1 in particular, an exemplary computing system environment, for instance, a medical information computing system, on which embodiments of the present invention may be implemented is illustrated and designated generally as reference numeral 100. It will be understood and appreciated by those of ordinary skill in the art that the illustrated medical information computing system environment 100 is merely an example of one suitable computing environment and is not intended to suggest any limitation as to the scope of use or functionality of the invention. Neither should the medical information computing system environment 100 be interpreted as having any dependency or requirement relating to any single component or combination of components illustrated therein.

Embodiments of the present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

Embodiments of the present invention may be described in the general context of computer-executable instructions, such as program modules, being executed by a computer. Generally, program modules include, but are not limited to, routines, programs, objects, components, and data structures that perform particular tasks or implement particular abstract data types. Embodiments of the present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 100 includes a general purpose computing device in the form of a server 102. Components of the server 102 may include, without limitation, a processing unit, internal system memory, and a suitable system bus for coupling various system components, including database cluster 104, with the server 102. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 102 typically includes, or has access to, a variety of computer readable media, for instance, database cluster 104. Computer readable media can be any available media that may be accessed by server 102, and includes volatile and nonvolatile media, as well as removable and non-removable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 22. Communication media typically embodies computer readable instructions, data structures, program modules, or other data in a modulated data signal, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 104, provide storage of computer readable instructions, data structures, program modules, and other data for the server 102.

The server 102 may operate in a computer network 106 using logical connections to one or more remote computers 108. Remote computers 108 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 28 may also be physically located in non-traditional medical care environments so that the entire health care community may be capable of integration on the network. The remote computers 108 may be personal computers, servers, routers, network PCs, mobile phones, peer devices, other common network nodes, or the like, and may include some or all of the components described above in relation to the server 102. The devices can be personal digital assistants or other like devices.

Exemplary computer networks 106 may include, without limitation, local area networks (LANs) and/or wide area networks (WANs). Such networking environments are commonplace in offices, enterprise-wide computer networks, intranets, and the Internet. When utilized in a WAN networking environment, the server 102 may include a modem or other means for establishing communications over the WAN, such as the Internet. In a networked environment, program modules or portions thereof may be stored in the server 102, in the database cluster 104, or on any of the remote computers 108. For example, and not by way of limitation, various application programs may reside on the memory associated with any one or more of the remote computers 108. It will be appreciated by those of ordinary skill in the art that the network connections shown are exemplary and other means of establishing a communications link between the computers (e.g., server 102 and remote computers 108) may be utilized.

In operation, a user may enter commands and information into the server 102 or convey the commands and information to the server 102 via one or more of the remote computers 108 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 102. In addition to a monitor, the server 102 and/or remote computers 108 may include other peripheral output devices, such as speakers and a printer.

Although many other internal components of the server 102 and the remote computers 108 are not shown, those of ordinary skill in the art will appreciate that such components and their interconnections are well known. Accordingly, additional details concerning the internal construction of the server 102 and the remote computers 108 are not further disclosed herein.

In accordance with embodiments of the present invention, a clinician may input a healthcare order relating to a particular patient into a computing device, such as exemplary remote computer 108 illustrated in FIG. 1. The computing device may be any device that is capable of receiving and/or presenting healthcare orders. Accordingly, the computing device may take on a variety of forms, such as a laptop computer, a mobile phone, a personal digital assistant (PDA), a server, or any other device that is capable of receiving and/or presenting healthcare orders. Clinicians include, but are not limited to, the treating physician, specialists such as surgeons, radiologists and cardiologists, emergency medical technicians, physician's assistants, nurse practitioners, nurses, nurse's aides, pharmacists, dieticians, microbiologists, laboratory experts, genetic counselors, researchers, veterinarians, students and the like A healthcare order, as used herein, is an item that was or is to be done for a particular patient. Healthcare orders may include, for example, administering a medication, monitoring vital signs, collecting data, performing a procedure and/or a test, or the like.

Once a clinician inputs a healthcare order, various other clinicians may need to be notified of the existence of the healthcare order. For instance, assume Dr. Howard inputs a healthcare order for Patient Sue to have her vital signs monitored every hour. Another clinician, e.g., Patient Sue's nurse, needs to know that Patient Sue must be monitored hourly. Additionally, the clinician that input the order may want to be notified when the order is completed. Thus, the computing device presents a notification to Patient Sue's nurse regarding the healthcare order. The notification may be an audible notification, a visual notification, a combination of an audible and a visual notification, or the like. The notification may, alternatively, be presented to any clinician associated with the patient of the healthcare order. Since clinicians may receive numerous notifications a day, the computing device may be programmed such that urgent notifications are presented in one manner (e.g., a tone or a vibration) while notifications that are not as urgent are presented in another manner (e.g., a flashing light).

In addition to being notified of an existing healthcare order, clinicians may also require status updates regarding a healthcare order. The computing device may present status notifications to the clinician that input the healthcare order or any other relevant clinician. By way of example only, a clinician may be notified that the healthcare order is pending, acknowledged, completed, or the like.

When results are associated with the healthcare order, the clinician may have the option to review the results, as illustrated in FIG. 2. FIG. 2 illustrates an illustrative graphical user interface display 200 of an electronic health record being accessed and reviewed. The interface 200 includes a medical record identifier 210 that identifies a patient, a patient location, and the like. The interface 200 further includes test results 220 that may be related to an input healthcare order. The test results 220 may be retrieved directly from the patient's EHR and displayed on a computing device. Additional information retrieved from an EHR may include a consultation request from a requesting clinician to seek a consult with a requested clinician.

Turning now to FIG. 3, a first exemplary method 300 for providing clinical information to clinicians is illustrated. It is identified in a patient's EHR that a first clinician (i.e., the requesting clinician) treating the patient has requested a consult with a second clinician (i.e., the requested clinician) at block 310. Clinicians often request consults with other clinicians in order to obtain a second opinion, seek guidance of a specialist, or the like.

A location for the first clinician is received at block 320 and a location for the second clinician is received at block 330. Clinician location information is monitored via clinician identifiers. Clinician identifiers may take the form of a security badge, an item attached to a security badge, or the like. The clinician identifiers are tracked by way of sensors located in the healthcare environment. The sensors may utilize ultrasound technology, infrared technology, radio-frequency identification (RFID) technology, or the like. Using said technology, the sensors send out signals to identifiers. An exemplary sensor system is the Cricket Indoor Location System sponsored by the MIT Project Oxygen partnership.

The signals are received by the identifiers and the identifiers respond to the signals. A response from an identifier is received by the sensors and the sensors are able to recognize and determine the location of the responding identifier. When a clinician identifier is identified by a sensor, the location for the clinician associated with the clinician identifier is updated. At block 340, a determination is made whether the location for the first clinician and the location for the second clinician are near one another. The determination is based on the proximity of the sensors that identified the location of both the first clinician and the second clinician. For example, the location of the sensors may be presented on the computing device via a blueprint of the healthcare environment. If Clinician 1 and Clinician 2 are identified by a sensor, their respective locations will be presented on the computing device. The computing device may access the actual location of the sensors within the healthcare environment and the distance between the sensors. Thus, the computing device is able to identify the sensors associated with the respective locations of Clinician 1 and Clinician 2 and determine whether the clinicians are near one another. The phrase "near one another," as used herein, generally refers to a pre-defined distance or proximity between two clinicians or any other individual and/or item associated with an identifier. A user may define "near one another" to be any variable that is appropriate for their use. For instance, a user may define being near one another as being on the same floor of a healthcare facility while another user may define being near one another as being on the same wing of a healthcare facility. Further examples of being near one another may include actual distance, e.g., 200 feet from one another.

Figures 4, 5:
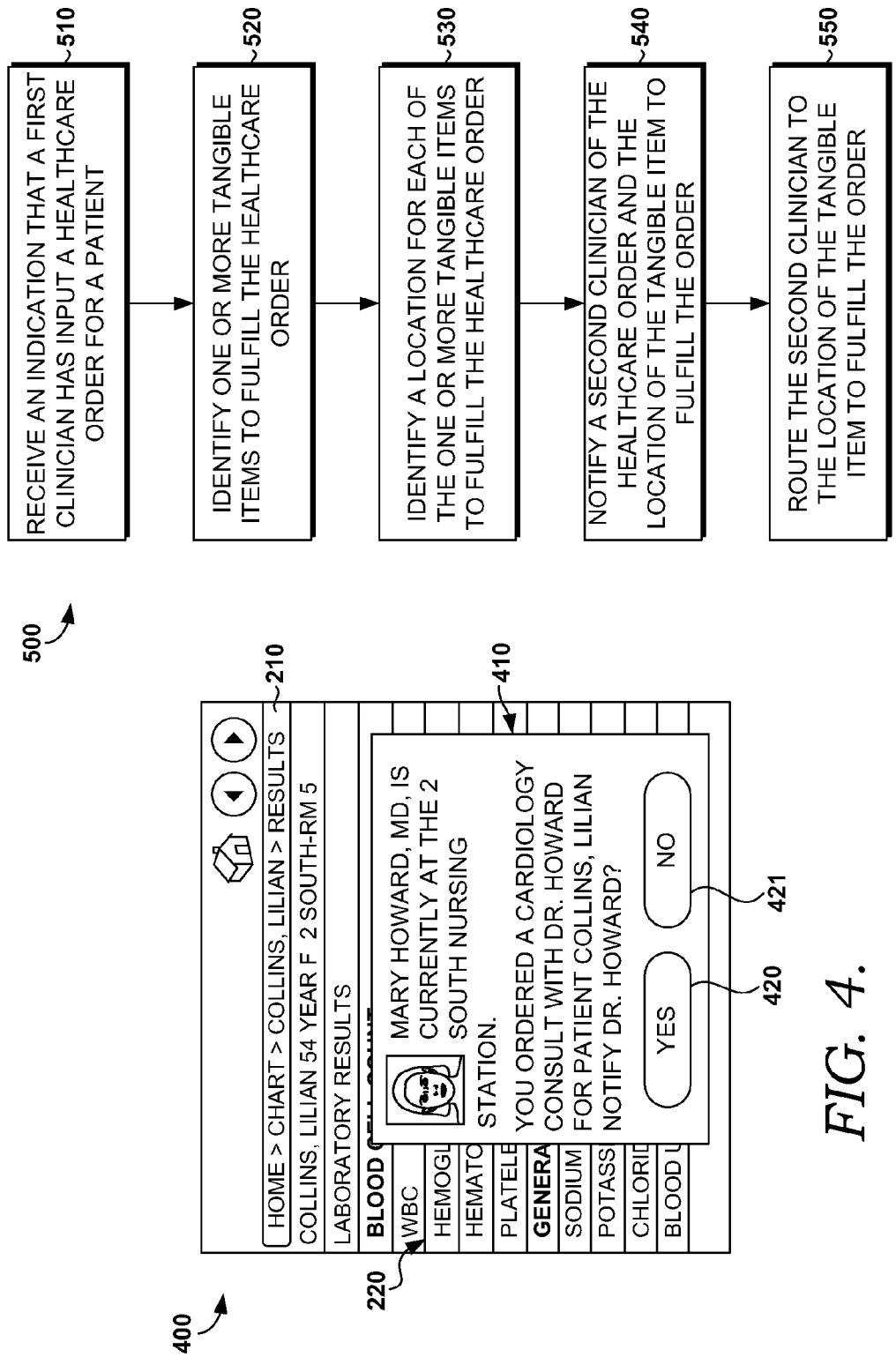
FIG. 4 is an illustrative graphical user interface display of a notification that a clinician is near a second clinician, in accordance with embodiments of the present invention.
FIG. 5 is a flow diagram illustrating a second exemplary method for providing clinical information to clinicians, in accordance with embodiments of the present invention.

Upon a determination that the location for the first clinician and the location for the second clinician are not near one another, the method ends at block 350. Upon a determination that the location for the first clinician and the location for the second clinician are near one another, a notification is presented to the first clinician that includes the location of the second clinician at block 360. An exemplary notification is illustrated in FIG. 4.

An illustrative user interface 400 may display test results 220 to a clinician and still present a notification 410. Notification 410 is presented to the clinician that Dr. Howard is nearby. Notification 410 may include the location for Dr. Howard (i.e., the requested or second clinician). Notification 410 may also include an affirmative indicator 420 and a negative indicator 421. Both the affirmative indicator 420 and the negative indicator 421 may be selected to indicate whether the clinician viewing the notification would like to inform the requested clinician, in this case, Dr. Howard, of their location. Such clinical integration makes it easier to identify clinicians' needs and facilitates communication between clinicians at convenient times. Less time is wasted tracking down colleagues since clinicians may be notified when their location is near that of a relevant clinician.

When the viewing clinician selects the affirmative indicator 420, a notification is presented to the requested clinician that includes the location of the viewing clinician. A selection of the affirmative indicator 420 also results in a date stamp and a time stamp of the selection such that the date and time of the notification is saved for reference. When the viewing clinician selects the negative indicator 421, a notification is not presented to the requested clinician at that time. A date stamp and a time stamp are still applied to the notification and saved in a database for reference.

In embodiments, the second clinician (i.e., the requested clinician) may be near the patient rather than near the first clinician. By way of example only, if Dr. Smith requested a consultation with Dr. Howard regarding Patient Ben and Dr. Howard is determined to be near Patient Ben, a notification will be sent to Dr. Smith such that Dr. Howard's proximity to the patient is known and an opportunity for the consultation is not lost.

A patient location is tracked in the same way as clinician location information. A patient identifier is associated with a patient and is identified by the plurality of sensors in the healthcare environment. The patient identifier may be a badge, a wristband, or any other method of monitoring the location of a person.

In other embodiments, a clinician may input a healthcare order into an EHR that requires one or more tangible items to fulfill the healthcare order. Many healthcare orders require one or more tangible items in order to be fulfilled. For example, a healthcare order to shave a patient requires a razor, shaving cream, a towel, and the like.

With reference to FIG. 5, a second exemplary method 500 for providing clinical information to clinicians is illustrated. An indication that a first clinician has input a healthcare order for a patient is received at block 510. At block 520, one or more tangible items required to fulfill the healthcare order are identified.

Orders requiring tangible items to be fulfilled may be fulfilled more efficiently when the required tangible item is easily located. Thus, at block 530 a location for each of the one or more tangible items required to fulfill the healthcare order is identified. Tangible items, much like clinicians, may be tracked via item identifiers. Item identifiers are similar to clinician identifiers in that they are tracked by way of the sensors located in the healthcare environment. The item identifiers may be tags on the items or any other method of monitoring the location of an item using the sensors.

When a location of the one or more tangible items required to fulfill the healthcare order is identified, a second clinician is notified of both the healthcare order and the location of the one or more tangible items required to fulfill the healthcare order at block 540. The second clinician may be a clinician associated with the patient, a clinician near the patient, a clinician identified to handle a particular healthcare order, or the like.

The location of the one or more tangible items required to fulfill the healthcare order may be presented to the second clinician via a blueprint of the healthcare environment. Thus, the nearest tangible item will be easily identified relative to the location of the second clinician, also tracked by the sensors by way of a clinician identifier. The nearest tangible item may also be determined relative to the location of the patient rather than to the location of the clinician.

The second clinician is then routed to the location of the one or more tangible items to fulfill the healthcare order at block 550. The directions to route the second clinician may be provided via a mobile computing device, such as a mobile phone. The directions may be presented using the blueprint of the healthcare environment, a list of turn-by-turn instructions, or a combination thereof. The second clinician may be routed to the nearest one or more tangible items to fulfill the healthcare order or, alternatively, the clinician may select a tangible item that is not illustrated as the nearest tangible item to fulfill the healthcare order.

With reference to FIG. 6, a third exemplary method 600 for providing clinical information to clinicians is illustrated. At block 610, an indication that a healthcare code is in effect for a patient is received. A location of the patient is identified at block 620. Patients are tracked in the same way as clinicians or tangible items. Patients may be associated with a patient identifier, which may be any mechanism that may be tracked via sensors in the healthcare environment.

Clinician location information is accessed at block 630. The location of each clinician is identified within the blueprint of the healthcare environment. Once clinician information is accessed, a nearest clinician relative to the location of the patient is identified at block 640. An alert is presented to the nearest clinician that the code is in effect for the patient at block 650. Such identification of a nearest clinician relative to a coding patient utilizes resources effectively to respond quickly to a coding patient. The alert may be an audible alert, a visual alert, a combination of an audible and a visual alert, or the like. The computing device presenting the alert may be programmed such that urgent alerts, such as a coding patient, are presented in one manner (e.g., a tone or a vibration) while alerts that are not as urgent are presented in another manner (e.g., a flashing light).

In addition to clinician use, the present invention may be utilized to optimize a clinical experience for a patient or an individual associated with a patient, such as a family member. The clinical experience is often overlooked for the individuals associated with the patient. Often times said individuals sit with a patient for endless hours to avoid leaving the patient's side and missing an important clinical event without ever being notified of an opportunity to be included in the clinical event. Embodiments of the present invention seek to alleviate the stress on said associated parties.

Privacy regulations provide that patient information is not shared with an unauthorized individual requesting said information. Thus, embodiments of the present invention are applicable to one or more individuals that are approved by the patient to receive notifications of clinical information. Thus, the patient must approve the individual seeking clinical information. The individual must also enable a computing device to receive the clinical information. Any web-enabled computing device may receive clinical information. The clinical information may be directly from the EHR or in the form of a notification and/or message.

Referring now to FIG. 7, a first exemplary method 700 for optimizing a clinical experience is illustrated. A location of a clinician associated with a patient is received at block 710 and a location of the patient is received at block 720. Clinicians and patients are both tracked via a clinician identifier and/or a patient identifier, respectively. The clinician may be associated with the patient by identification in the EHR. The clinician may also be associated with the patient as a requested clinician, e.g., a consult with the requested clinician has been documented in the EHR.

Once the location of the clinician and the location of the patient are received, a determination is made whether the clinician is near the patient at block 730. A clinician is determined to be near a patient based on the proximity of the sensors that identify the clinician identifier and the patient identifier. An administrator may input a predefined threshold such that a clinician is determined to be near a patient if the distance between the clinician identifier and the patient identifier is below the predefined threshold. Alternatively, the nearest clinician is determined without using a predefined threshold.

If the clinician is not determined to be near the patient, the method ends at block 740. If the clinician is determined to be near the patient, a notification is communicated to a non-present party that the clinician is near the patient at block 750. A non-present party may be any individual associated with a patient that is approved to receive notifications regarding a patient's healthcare experience. For example, family members may be approved as non-present parties in addition to close friends, guardians, and the like.

By way of example only, assume that a non-present party (e.g., a family member) has left the patient's room to go to a vending machine. The non-present party would like to be notified if the patient's clinician is near the patient. A mobile computing device may receive said notification such that the non-present party does not miss an opportunity to speak to the clinician, to be present when the clinician visits the patient, and the like.

The non-present party may or may not be tracked via an identifier in the same way as patients and clinicians are tracked. The present invention may include predefined locations to aid navigation such that it is not necessary that a non-present party be tracked. The non-present party may simply identify their location and utilize the present invention in the same way as if they were being tracked. If the non-present party is presented with turn-by-turn directions then the steps will update upon receiving an indication from the user to proceed to the next step. Alternatively, the non-present party could be tracked via the plurality of sensors and the directions may automatically update as the non-present party's location is updated from passing a sensor.

Referring now to FIG. 8, a second exemplary method 800 for optimizing a clinical experience is illustrated. Initially, at block 810, a notification that a clinician associated with a patient is near the patient is received. The notification may identify the patient, the clinician, the location of the clinician, the location of the patient, and the like. The notification may also present a selectable return indicator to return to the patient, the patient's room, and the like, as illustrated in FIG. 9.

The notification is presented to a non-present party at block 820. The notification may be presented on a mobile computing device, such as a mobile phone, such that an individual may use their personal mobile phone that is enabled with the present invention to be notified of clinical events. For example, a non-present party that is associated with a patient may have their personal mobile phone activated to receive notifications regarding clinical events of the patient. Thus, no additional devices are required since individuals' personal devices may be configured to be compatible with embodiments of the present invention.

An indication is received from the non-present party to return to the patient at block 830. The indication is received upon selection of the selectable return indicator to return to the patient. FIG. 9 illustrates a graphical user interface 900 including a notification 910 presented to the non-present party that includes a selectable return indicator 920 to return to the patient. Notification 910 identifies the clinician and presents a message that the clinician is near the patient. Selectable return indicator 920 is also presented such that selection thereof routes the non-present party back to the patient.

Upon selection of the selectable return indicator 920, a user receives directions to return to the patient. Turn-by-turn directions are presented to the non-present party at block 840 to route the non-present party back to the patient. The turn-by-turn directions may be presented in combination with a blueprint of the healthcare environment.

In addition to the above-described embodiments, the computing device utilized for the present invention may perform other functions to optimize the clinical experience. Navigational directions of a healthcare environment are accessible to a user, as described above, and points of interest and directions thereto may also be identified and presented on the computing device. A point of interest is a location external to that of the healthcare environment. For example, a user may need to find a nearby bank, restaurant, pharmacy, or the like. The computing device, once activated to perform the present invention, will identify a desired point of interest and present directions that route the user to the point of interest.

Further, the computing device may be used to communicate messages between a plurality of users. For instance, a patient may want to ask a clinician a question immediately and does not want to wait until the clinician is present. The patient could input the message into a computing device and the message would be presented to the clinician.

A patient may also utilizing the computing device to manager their after-care. Notifications regarding their current healthcare status may be communicated to the patient. For example, a patient may be notified when the pharmacy has completed their prescription and it is ready for pick-up. A patient may also review upcoming scheduled tests and previous test results from their electronic health record.

Additionally, a patient may schedule follow-up appointments in the computing device. The patient may also be notified of the follow-up appointment. Upon returning for the follow-up appointment, a reason is identified for the follow-up appointment from the patient's EHR. Once the reason for the clinical visit is identified, the computing device may be configured such that an advertisement relevant to the clinical visit is presented to the user. For example, a patient may return to for a follow-up appointment for diabetes treatment. A relevant advertisement for a new pharmaceutical used to treat diabetes may be presented.

Alerts that a code is in effect may be communicated to users of the computing device including patients, clinicians, and non-present parties. For instance, a patient may be coding and a clinician would be notified of the code and the location of the patient. Further, a code red (i.e., a fire) may be in effect for the healthcare environment. Non-present parties and patients greatly benefit from being notified of the code's meaning and an evacuation route presented on the display of the computing device.

As can be understood, the present invention provides computer-storage media, systems, and methods for providing clinical information to clinicians. Embodiments of the present invention may also provide computer-storage media, systems, and methods for optimizing a clinical experience.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

Having thus described the invention, what is claimed is:

1. One or more tangible computer-storage media having computer-useable instructions embodied thereon that, when executed, perform a method for providing clinical information to clinicians, the method comprising:
   identifying in a patient's electronic health record that a first clinician treating the patient has requested a consult with a second clinician treating the patient;
   receiving a location for the first clinician by way of a first clinician identifier, wherein the first clinician identifier is tracked via a plurality of sensors in a healthcare environment, and wherein the plurality of sensors utilize one of ultrasound technology, infrared technology, or radio-frequency identification technology;
   receiving a location for the second clinician by way of a second clinician identifier, wherein the second clinician identifier is tracked via the plurality of sensors in the healthcare environment;
   determining whether the location for the first clinician and the location for the second clinician are within a predefined distance from one another, wherein the determination is based on the proximity of the sensors that identified the location of both the first and the second clinician; and
   upon determining that the location for the first clinician and the location for the second clinician are within the predefined distance from one another, presenting a notification to the first clinician that includes both the location of the second clinician and the consult requested by the first clinician.

2. The computer-storage media of claim 1, wherein the method further comprises:
   presenting the notification to the first clinician via a mobile device.

3. The computer-storage media of claim 2, wherein the method further comprises:
   presenting the first clinician with an option to inform the second clinician of the location of the first clinician.

4. The computer storage media of claim 3, wherein the method further comprises:
   receiving an indication from the clinician to inform the second clinician of the location of the first clinician.

5. The computer-storage media of claim 4, wherein the method further comprises:
   presenting a notification to the second clinician that includes the location of the first clinician.

6. The computer-storage media of claim 1, wherein the method further comprises notifying an ordering clinician that an order is complete.

7. The computer-storage media of claim 1, wherein the method further comprises presenting status updates of an order via a mobile device.

8. The computer-storage media of claim 7, wherein status updates include an indication that a result is available, an indication that a test is in progress, or an indication that the test is pending.

* * * * *